(12) United States Patent
Wang et al.

(10) Patent No.: US 7,923,022 B2
(45) Date of Patent: *Apr. 12, 2011

(54) DEGRADABLE POLYMERIC IMPLANTABLE MEDICAL DEVICES WITH CONTINUOUS PHASE AND DISCRETE PHASE

(75) Inventors: Yunbing Wang, Sunnyvale, CA (US); David C. Gale, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1029 days.

This patent is subject to a terminal disclaimer.

(21) Appl. No.: 11/521,271

(22) Filed: Sep. 13, 2006

(65) Prior Publication Data

US 2008/0063685 A1    Mar. 13, 2008

(51) Int. Cl.
*A61F 2/02* (2006.01)
*A61F 2/00* (2006.01)

(52) U.S. Cl. ............... 424/426; 525/437; 623/11.11; 623/23.64; 623/23.7; 623/23.75

(58) Field of Classification Search .................. None
See application file for complete search history.

(56) References Cited

U.S. PATENT DOCUMENTS

| | | | |
|---|---|---|---|
| 3,458,602 A * | 7/1969 | Pollock .................... | 525/243 |
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,744,365 A * | 5/1988 | Kaplan et al. .............. | 606/230 |
| 4,768,507 A | 9/1988 | Fischell et al. | |
| 4,776,337 A | 10/1988 | Palmaz | |
| 4,800,882 A | 1/1989 | Gianturco | |
| 4,816,339 A | 3/1989 | Tu et al. | |
| 4,818,559 A | 4/1989 | Hama et al. | |
| 4,844,854 A | 7/1989 | Kaplan et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,104,410 A | 4/1992 | Chowdhary | |
| 5,108,417 A | 4/1992 | Sawyer | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |

(Continued)

FOREIGN PATENT DOCUMENTS

DE    44 07 079    9/1994

(Continued)

OTHER PUBLICATIONS

Wang, J.Poly.Sci: Part A: Polymer Chemistry, vol. 39, 2001.*
International Search Report for PCT/US2007/019507, mailed Feb. 10, 2009, 7 pgs.
U.S. Appl. No. 10/317,435, filed Aug. 17, 2010, Hossainy et al.
Anonymous, *Bioabsorbable stent mounted on a catheter having optical coherence tomography capabilities*, Research Disclosure, Sep. 2004, pp. 1159-1162.

(Continued)

*Primary Examiner* — Robert A Wax
*Assistant Examiner* — William Craigo
(74) *Attorney, Agent, or Firm* — Squire, Sanders & Dempsey (US) LLP

(57) ABSTRACT

An implantable medical device is disclosed comprising: a structural element, wherein the structural element includes: a continuous phase comprising a first polymer of LPLG; a discrete phase within the continuous phase, wherein the discrete phase comprises a second polymer including rapidly eroding elastic discrete phase segments. The second polymer further includes anchor segments that have the same or substantially the same chemical make up as the first polymer of the continuous phase, and at least some of the anchor segments have partially or completely phase-separated from the discrete phase into the continuous phase.

31 Claims, 4 Drawing Sheets

U.S. PATENT DOCUMENTS

| | | | |
|---|---|---|---|
| 5,279,594 A | 1/1994 | Jackson | |
| 5,282,860 A | 2/1994 | Matsuno et al. | |
| 5,289,831 A | 3/1994 | Bosley | |
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A | 8/1994 | Jarrett et al. | |
| 5,342,621 A | 8/1994 | Eury | |
| 5,356,433 A | 10/1994 | Rowland et al. | |
| 5,383,925 A | 1/1995 | Schmitt | |
| 5,385,580 A | 1/1995 | Schmitt | |
| 5,389,106 A | 2/1995 | Tower | |
| 5,399,666 A | 3/1995 | Ford | |
| 5,423,885 A | 6/1995 | Williams | |
| 5,441,515 A | 8/1995 | Khosravi et al. | |
| 5,443,458 A | 8/1995 | Eury | |
| 5,443,500 A | 8/1995 | Sigwart | |
| 5,455,040 A | 10/1995 | Marchant | |
| 5,464,650 A | 11/1995 | Berg et al. | |
| 5,475,063 A * | 12/1995 | Kaplan et al. | 525/411 |
| 5,502,158 A | 3/1996 | Sinclair et al. | |
| 5,514,379 A | 5/1996 | Weissleder et al. | |
| 5,527,337 A | 6/1996 | Stack et al. | |
| 5,545,408 A | 8/1996 | Trigg et al. | |
| 5,554,120 A | 9/1996 | Chen et al. | |
| 5,556,413 A | 9/1996 | Lam | |
| 5,578,046 A | 11/1996 | Liu et al. | |
| 5,578,073 A | 11/1996 | Haimovich et al. | |
| 5,591,199 A | 1/1997 | Porter et al. | |
| 5,591,607 A | 1/1997 | Gryaznov et al. | |
| 5,593,403 A | 1/1997 | Buscemi | |
| 5,593,434 A | 1/1997 | Williams | |
| 5,599,301 A | 2/1997 | Jacobs et al. | |
| 5,599,922 A | 2/1997 | Gryaznov et al. | |
| 5,605,696 A | 2/1997 | Eury et al. | |
| 5,607,442 A | 3/1997 | Fischell et al. | |
| 5,607,467 A | 3/1997 | Froix | |
| 5,618,299 A | 4/1997 | Khosravi et al. | |
| 5,629,077 A | 5/1997 | Turnlund et al. | |
| 5,631,135 A | 5/1997 | Gryaznov et al. | |
| 5,632,771 A | 5/1997 | Boatman et al. | |
| 5,632,840 A | 5/1997 | Campbell | |
| 5,637,113 A | 6/1997 | Tartaglia et al. | |
| 5,641,501 A | 6/1997 | Cooper et al. | |
| 5,649,977 A | 7/1997 | Campbell | |
| 5,667,767 A | 9/1997 | Greff et al. | |
| 5,667,796 A | 9/1997 | Otten | |
| 5,670,558 A | 9/1997 | Onishi et al. | |
| 5,674,286 A * | 10/1997 | D'Alessio et al. | 424/423 |
| 5,693,085 A | 12/1997 | Buirge et al. | |
| 5,700,286 A | 12/1997 | Tartaglia et al. | |
| 5,707,385 A | 1/1998 | Williams | |
| 5,711,763 A | 1/1998 | Nonami et al. | |
| 5,716,981 A | 2/1998 | Hunter et al. | |
| 5,725,549 A | 3/1998 | Lam | |
| 5,726,297 A | 3/1998 | Gryaznov et al. | |
| 5,728,751 A | 3/1998 | Patnaik | |
| 5,733,326 A | 3/1998 | Tomonto et al. | |
| 5,733,330 A | 3/1998 | Cox | |
| 5,733,564 A | 3/1998 | Lehtinen | |
| 5,733,925 A | 3/1998 | Kunz et al. | |
| 5,741,881 A | 4/1998 | Patnaik | |
| 5,756,457 A | 5/1998 | Wang et al. | |
| 5,756,476 A | 5/1998 | Epstein et al. | |
| 5,765,682 A | 6/1998 | Bley et al. | |
| 5,766,204 A | 6/1998 | Porter et al. | |
| 5,766,239 A | 6/1998 | Cox | |
| 5,766,710 A | 6/1998 | Turnlund et al. | |
| 5,769,883 A | 6/1998 | Buscemi et al. | |
| 5,780,807 A | 7/1998 | Saunders | |
| 5,800,516 A | 9/1998 | Fine et al. | |
| 5,811,447 A | 9/1998 | Kunz et al. | |
| 5,824,049 A | 10/1998 | Ragheb et al. | |
| 5,830,178 A | 11/1998 | Jones et al. | |
| 5,830,461 A | 11/1998 | Billiar | |
| 5,830,879 A | 11/1998 | Isner | |
| 5,833,651 A | 11/1998 | Donovan et al. | |
| 5,834,582 A | 11/1998 | Sinclair et al. | |
| 5,836,962 A | 11/1998 | Gianotti | |
| 5,837,313 A | 11/1998 | Ding et al. | |
| 5,837,835 A | 11/1998 | Gryaznov et al. | |
| 5,840,083 A | 11/1998 | Braach-Maksvytis | |
| 5,851,508 A | 12/1998 | Greff et al. | |
| 5,853,408 A | 12/1998 | Muni | |
| 5,854,207 A | 12/1998 | Lee et al. | |
| 5,855,612 A | 1/1999 | Ohthuki et al. | |
| 5,855,618 A | 1/1999 | Patnaik et al. | |
| 5,858,746 A | 1/1999 | Hubbell et al. | |
| 5,865,814 A | 2/1999 | Tuch | |
| 5,868,781 A | 2/1999 | Killion | |
| 5,873,904 A | 2/1999 | Ragheb et al. | |
| 5,874,101 A | 2/1999 | Zhong et al. | |
| 5,874,109 A | 2/1999 | Ducheyne et al. | |
| 5,874,165 A | 2/1999 | Drumheller | |
| 5,874,509 A * | 2/1999 | Shalaby et al. | 526/194 |
| 5,876,743 A | 3/1999 | Ibsen et al. | |
| 5,877,263 A | 3/1999 | Patnaik et al. | |
| 5,879,713 A | 3/1999 | Roth et al. | |
| 5,888,533 A | 3/1999 | Dunn | |
| 5,891,192 A | 4/1999 | Murayama et al. | |
| 5,897,955 A | 4/1999 | Drumheller | |
| 5,906,759 A | 5/1999 | Richter | |
| 5,914,182 A | 6/1999 | Drumheller | |
| 5,916,870 A | 6/1999 | Lee et al. | |
| 5,922,005 A | 7/1999 | Richter et al. | |
| 5,942,209 A | 8/1999 | Leavitt et al. | |
| 5,948,428 A | 9/1999 | Lee et al. | |
| 5,954,744 A | 9/1999 | Phan et al. | |
| 5,957,975 A | 9/1999 | Lafont et al. | |
| 5,965,720 A | 10/1999 | Gryaznov et al. | |
| 5,971,954 A | 10/1999 | Conway et al. | |
| 5,976,182 A | 11/1999 | Cox | |
| 5,980,564 A | 11/1999 | Stinson | |
| 5,980,928 A | 11/1999 | Terry | |
| 5,980,972 A | 11/1999 | Ding | |
| 5,981,568 A | 11/1999 | Kunz et al. | |
| 5,986,169 A | 11/1999 | Gjunter | |
| 5,997,468 A | 12/1999 | Wolff et al. | |
| 6,010,445 A | 1/2000 | Armini et al. | |
| 6,015,541 A | 1/2000 | Greff et al. | |
| 6,042,875 A | 3/2000 | Ding et al. | |
| 6,048,964 A | 4/2000 | Lee et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,066,156 A | 5/2000 | Yan | |
| 6,071,266 A | 6/2000 | Kelley | |
| 6,074,659 A | 6/2000 | Kunz et al. | |
| 6,080,177 A | 6/2000 | Igaki et al. | |
| 6,080,488 A | 6/2000 | Hostettler et al. | |
| 6,083,258 A | 7/2000 | Yadav | |
| 6,093,463 A | 7/2000 | Thakrar | |
| 6,096,070 A | 8/2000 | Ragheb et al. | |
| 6,096,525 A | 8/2000 | Patnaik | |
| 6,099,562 A | 8/2000 | Ding et al. | |
| 6,103,230 A | 8/2000 | Billiar et al. | |
| 6,107,416 A | 8/2000 | Patnaik et al. | |
| 6,110,188 A | 8/2000 | Narciso, Jr. | |
| 6,113,629 A | 9/2000 | Ken | |
| 6,117,979 A | 9/2000 | Hendriks et al. | |
| 6,120,536 A | 9/2000 | Ding et al. | |
| 6,120,904 A | 9/2000 | Hostettler et al. | |
| 6,121,027 A | 9/2000 | Clapper et al. | |
| 6,125,523 A | 10/2000 | Brown et al. | |
| 6,127,173 A | 10/2000 | Eckstein et al. | |
| 6,129,761 A | 10/2000 | Hubbell | |
| 6,129,928 A | 10/2000 | Sarangapani et al. | |
| 6,150,630 A | 11/2000 | Perry et al. | |
| 6,153,252 A | 11/2000 | Hossainy et al. | |
| 4,776,337 A | 12/2000 | Palmaz | |
| 6,159,951 A | 12/2000 | Karpeisky et al. | |
| 6,160,084 A | 12/2000 | Langer et al. | |
| 6,165,212 A | 12/2000 | Dereume et al. | |
| 6,166,130 A | 12/2000 | Rhee et al. | |

| | | |
|---|---|---|
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,228,954 B1* | 5/2001 | Kaplan et al. ............... 525/411 |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,299,631 B1 | 10/2001 | Shalaby |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0139567 A1 | 7/2003 | Kim et al. |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |
| 2004/0254639 A1* | 12/2004 | Li et al. .................... 623/1.49 |
| 2007/0231365 A1* | 10/2007 | Wang et al. .................... 424/426 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |
| WO | WO 2007/126598 | 11/2007 |
| WO | WO 2007126598 A2 * | 11/2007 |
| WO | WO 2008/016667 | 2/2008 |

OTHER PUBLICATIONS

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., Sutureless Anastomosis of the Small Intestine and the Colon in Pigs Using an Absorbable Intraluminal Stent and Fibrin Glue, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, Vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Van Vlack, *Elements of Materials Science and Engineering*, Addison-Wesley, pp. 270-271, (1989).

Völkel et al., *Targeting of immunoliposomes to endothelial cells using a single-chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Wang et al., J. Polymer Science PartA:Polymer Chem., 26, 2001.

Yau et al., Modern Size-Exclusion Liquid Chromatography, Wiley-Interscience Publication, IX-XV (1979).

\* cited by examiner

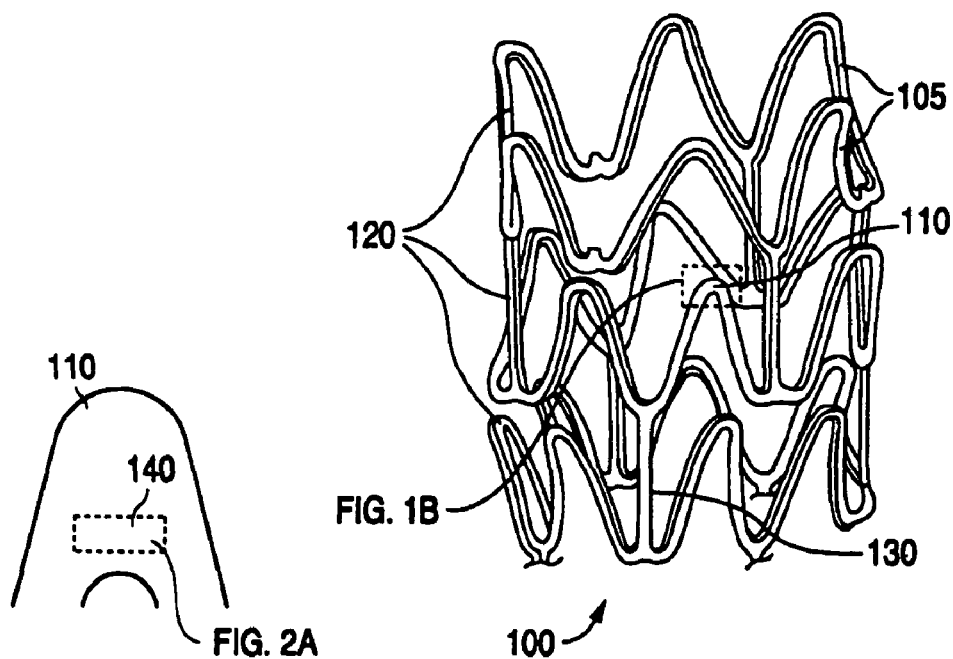
FIG. 1B  FIG. 1A
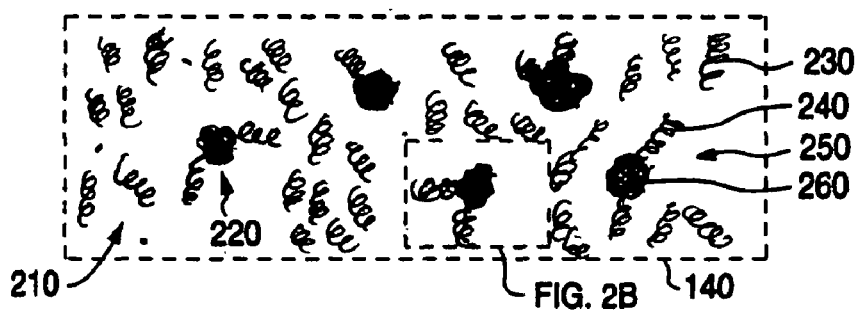
FIG. 2A
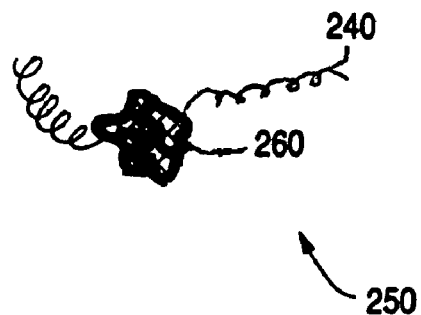
FIG. 2B

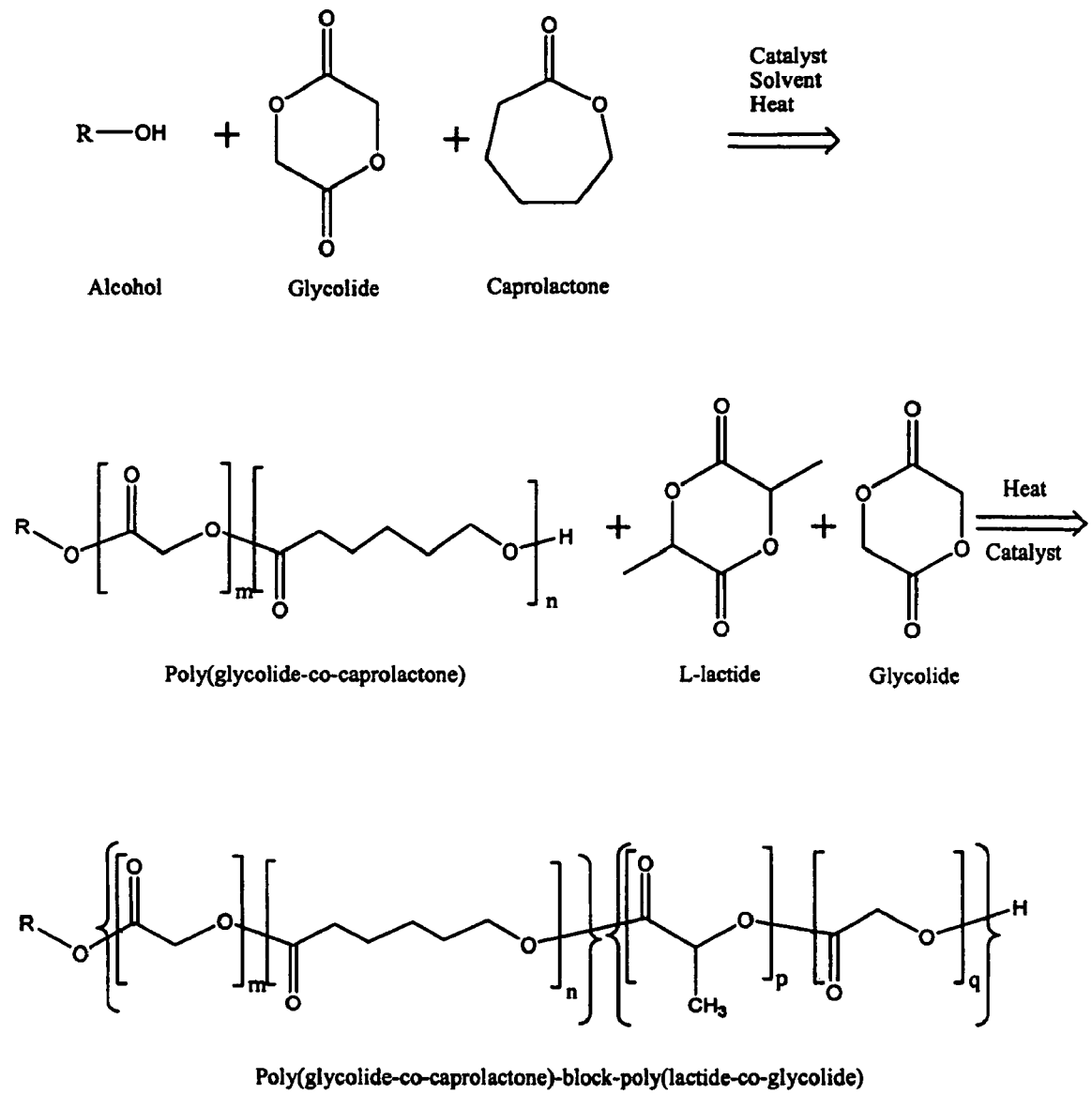
Figure 5 Synthesis of P(GA-co-CL)-b-LPLG

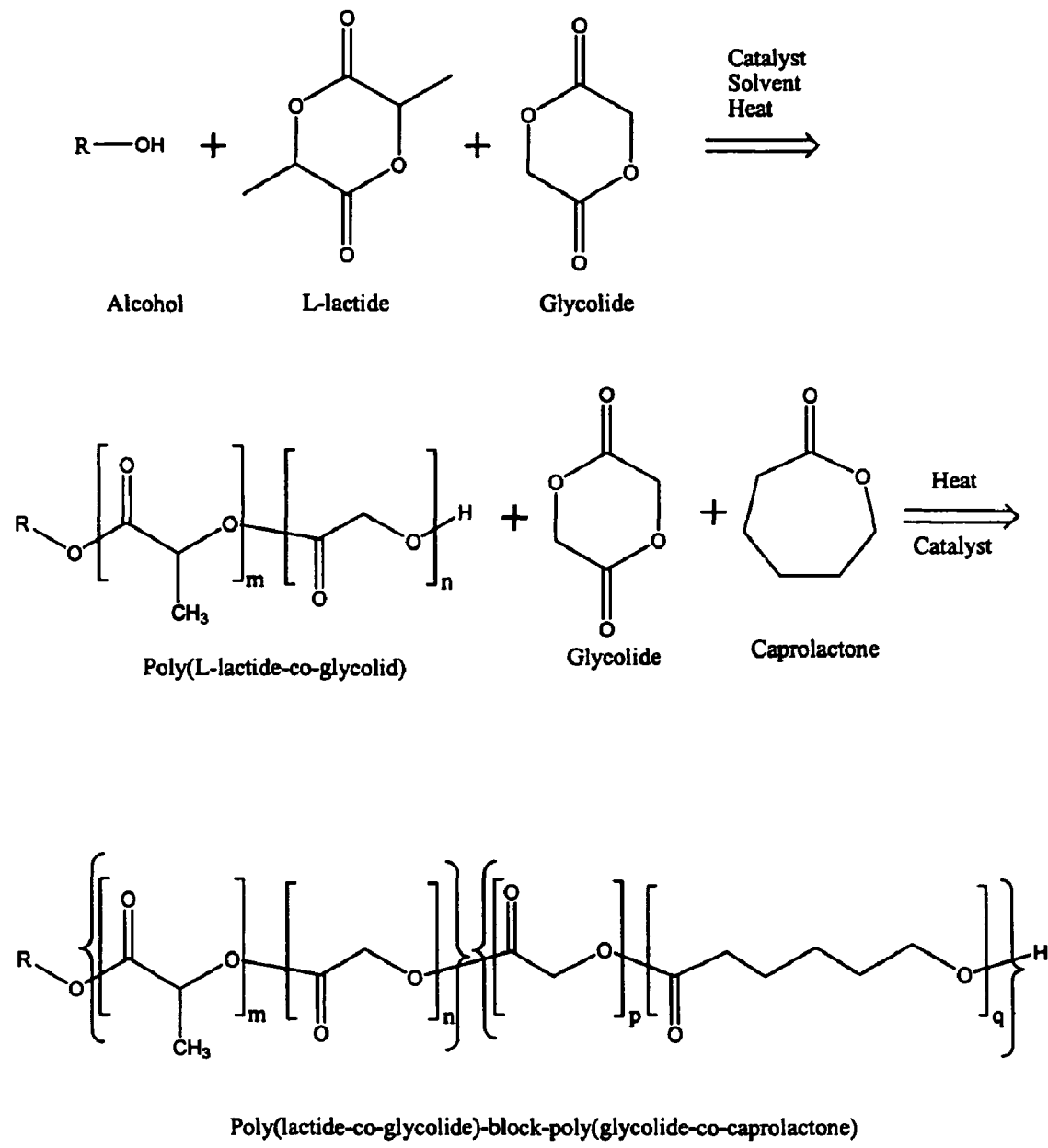
Figure *b* Synthesis of LPLG-b-P(GA-co-CL)

DEGRADABLE POLYMERIC IMPLANTABLE MEDICAL DEVICES WITH CONTINUOUS PHASE AND DISCRETE PHASE

BACKGROUND OF THE INVENTION

1. Field of the Invention

This invention relates to a degradable polymeric implantable medical device.

2. Description of the State of the Art

This invention relates generally to implantable medical devices having a range of mechanical and therapeutic requirements during use. In particular, the invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

The treatment of a diseased site or lesion with a stent involves both delivery and deployment of the stent. "Delivery" refers to introducing and transporting the stent through a bodily lumen to the treatment site in a vessel. "Deployment" corresponds to the expanding of the stent within the lumen at the treatment site. Delivery and deployment of a stent are accomplished by positioning the stent at one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to satisfy several mechanical requirements. First, the stent must be capable of withstanding the structural loads, namely radial compressive forces, imposed on the stent as it supports the walls of a vessel lumen. This requires a sufficient degree of strength and rigidity or stiffness. In addition to having adequate radial strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of portions of the stent. Once expanded, the stent must maintain its size and shape throughout its service life despite the various forces that may come to bear thereon, including the cyclic loading induced by the beating heart. Therefore, a stent must be capable of exhibiting relatively high toughness which corresponds to high strength and rigidity, as well as flexibility.

A stent is typically composed of scaffolding that includes a pattern or network of interconnecting structural elements or struts. The scaffolding can be formed of wires, tubes, or sheets of material rolled into a cylindrical shape. The scaffolding is designed to allow the stent to be radially expandable. The pattern is generally designed to maintain the longitudinal flexibility and radial rigidity required of the stent. Longitudinal flexibility facilitates delivery of the stent and radial rigidity is needed to hold open a bodily lumen. A medicated stent may be fabricated by coating the surface of either a metallic or polymeric scaffolding with a polymeric carrier that includes a bioactive agent. Polymeric scaffolding may also serve as a carrier of bioactive agent.

It may be desirable for a stent to be biodegradable. In many treatment applications, the presence of a stent in a body may be necessary for a limited period of time until its intended function, for example, maintaining vascular patency and/or drug delivery is accomplished. Thus, stents are often fabricated from biodegradable, bioabsorbable, and/or bioerodable materials such that they completely erode only after the clinical need for them has ended. In addition, a stent should also be capable of satisfying the mechanical requirements discussed above during the desired treatment time.

A polymeric implantable medical device should be mechanically stable throughout the range of stress experienced during use. Unfortunately, many polymers used for stent scaffoldings and coatings are relatively brittle under physiological conditions, e.g., at body temperature. Many polymers remain relatively brittle, and hence susceptible to mechanical instability such as fracturing while in the body. In addition to mechanical stability, a device should have a sufficient rate of biodegradability or erosion as dictated by use.

SUMMARY

An implantable medical device comprising: a structural element, wherein the structural element includes: a continuous phase comprising a first polymer of LPLG; a discrete phase within the continuous phase, wherein the discrete phase comprises a second polymer including discrete phase segments; the second polymer further includes anchor segments that have the same or substantially the same chemical make up as the first polymer of the continuous phase, and at least some of the anchor segments have partially or completely phase-separated from the discrete phase into the continuous phase.

Further, disclosed herein is an implantable medical device, comprising a structural element fabricated of a blend that includes about 60 to about 99 wt % of a first polymer of LPLG, wherein the first polymer forms a continuous phase; and about 1 to about 40 wt % of a second polymer, the second polymer forming a discrete phase within the continuous phase, wherein the second polymer having a Tg below body temperature comprises discrete phase segments that degrade to acidic fragments, the second polymer also comprises anchor segments having the same or substantially the same chemical make up as the continuous phase, wherein the anchor segment has phase-separated out from the discrete phase into the continuous phase.

Further, disclosed herein is an implantable medical device, comprising a structural element fabricated of a blend that includes: about 70 to about 95 wt % of a first polymer LPLG, wherein the first polymer forms a continuous phase; about 1 to about 10 wt % of a second polymer, the second polymer forming a discrete phase within the continuous phase, the second polymer comprising discrete phase segments and anchor segments, wherein anchor segments have the same or substantially the same chemical make up as the first polymer of the continuous phase and have phase-separated out from the discrete phase into the continuous phase; and about 5 to about 30 wt % of a third polymer having a Tg below body temperature consisting essentially of discrete phase segments, wherein the third polymer degrades into fragments at least some of which are acidic.

Further, disclosed herein is an implantable medical device, comprising: about 60 to about 99 wt % of a first polymer having the chemical structure:

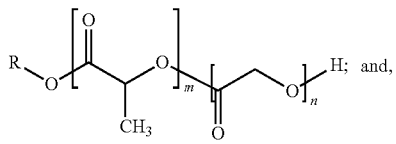

about 1 to about 40 wt % of a second polymer having the chemical structure:

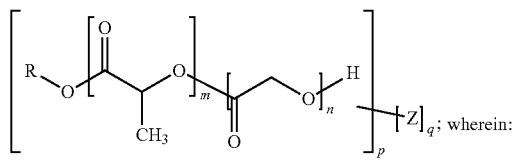

Z is a polymer with a $T_g$ below body temperature that degrades into fragments at least some of which are acidic; wherein:

the first polymer forms a continuous phase;

the "Z" polymer forms a discrete phase within the continuous phase; and, the "p" segment of the second polymer partially or completely phase-separates out from the discrete phase into the continuous phase.

Further, disclosed herein is a composition comprising: a continuous phase comprising a first polymer of LPLG; a discrete phase within the continuous phase, wherein the discrete phase comprises a second polymer including discrete phase segments;

the second polymer further includes anchor segments that have the same or substantially the same chemical make up as the first polymer of the continuous phase, and at least some of the anchor segments have partially or completely phase-separated from the discrete phase into the continuous phase.

Further, disclosed herein is a method of forming a copolymer comprising: mixing glycolide monomers, caprolactone monomers, a catalyst, and a solvent to form a solution, wherein the glycolide and caprolactone monomers react in the solution to form P(GA-co-CL); and adding L-lactide monomers and glycolide monomers and allowing monomers to react with P(GA-co-CL) to form P(GA-co-CL)-b-LPLG.

Further, disclosed herein is a method of forming a copolymer comprising: mixing glycolide monomers, L-lactide monomers, a catalyst, and a solvent to form a solution, wherein the glycolide and L-lactide monomers react in the solution to form LPLG; and adding caprolactone monomers and glycolide monomers and allowing monomers to react with LPLG to form LPLG-b-P(GA-co-CL).

Still further, the invention includes a copolymer comprising LPLG-b-P(GA-co-CL).

Finally, the invention includes a copolymer comprising P(GA-co-CL)-b-LPLG.

BRIEF DESCRIPTION OF DRAWINGS

FIG. 1A depicts a stent made up of struts.

FIG. 1B depicts a view of a sidewall of a segment of a strut of FIG. 1A.

FIG. 2A depicts a close-up view of the strut of FIG. 1B showing a continuous phase and a discrete phase.

FIG. 2B depicts a close-up view of a second polymer as shown in FIG. 2A that makes up the discrete phase.

FIG. 5 depicts the synthesis of P(GA-co-CL)-b-LPLG copolymer according to one embodiment of the invention.

FIG. 6 depicts the synthesis of poly(lactide-co-glycolide)-b-poly(glycolide-co-caprolactone) copolymer ("LPLG-b-P(GA-co-CL)") copolymer according to another embodiment of the invention.

DETAILED DESCRIPTION

Figure 3:
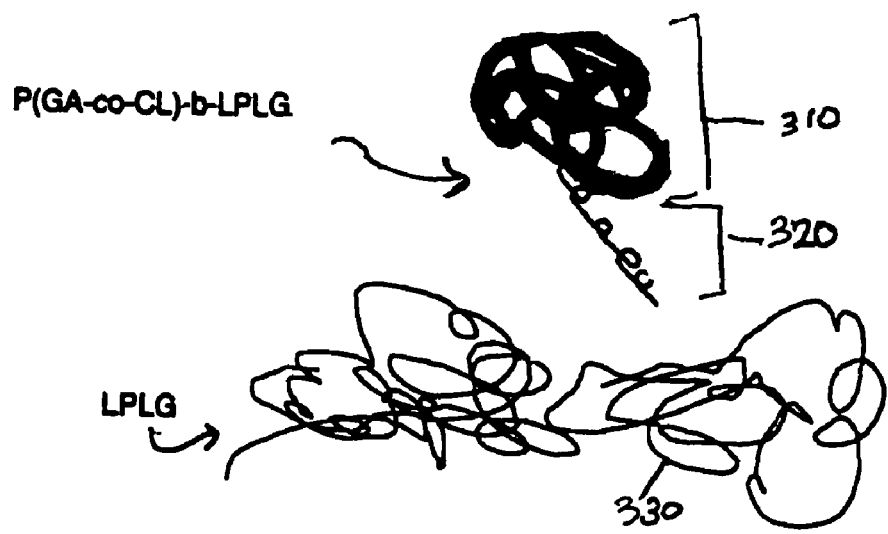
FIG. 3 conceptually illustrates a binary blend of poly(glycolide-co-caprolactone)-b-poly(L-lactide-co-glycolide) copolymer ("P(GA-co-CL)-b-LPLG") and poly(L-lactide-co-glycolide) copolymer ("LPLG").

Various embodiments of the present invention relate to composite implantable medical devices configured to have particular mechanical properties such as strength and flexibility. Embodiments of the present invention also relate to composite devices with particular degradation characteristics. A composite implantable medical device is a device which is made up of two or more macroscopically distinct materials or phases that have different properties. The composite device as a whole may have desirable properties of two or more of the distinct materials or phases. Therefore, desirable mechanical and/or degradation properties in an implantable medical device may be obtained through the use of a polymer composite structure.

For the purposes of the present invention, the following terms and definitions apply:

The "glass transition temperature," $T_g$, of a polymer is the temperature at which the polymer's amorphous domains transform from a brittle vitreous state to a solid deformable or ductile state at atmospheric pressure. In other words, $T_g$ corresponds to the temperature where segmental motion starts in the polymer chains. When an amorphous or semicrystalline polymer is exposed to an increasing temperature, both the polymer's coefficient of expansion and heat capacity increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Solvent" is defined as a substance capable of dissolving or dispersing one or more other substances or capable of at least partially dissolving or dispersing the substance(s) to form a uniform mixture at the molecular- or ionic-size level at selected temperatures and pressures. It should be noted that some solvents can only dissolve glycolide monomers at temperatures above ambient temperature (15° C. to 30° C.). Also, a solvent may include a blend of solvents.

"Dissolve" refers to a substance passing into solution on a molecular scale with or without chemical breakdown of the substance.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). Compressive stress is a normal component of stress applied to materials resulting in their compaction (decrease in length).

"Expansion" or "compression" is defined as the increase or decrease in length of a sample of material when the sample is subjected to stress.

"Strain" refers to the amount of expansion or compression that occurs in a material at a given stress. Strain is expressed as a fraction or percentage of the original length, i.e., the change in length divided by the original length. Strain, therefore, is positive for expansion and negative for compression.

A property of a material that quantifies a degree of strain with applied stress is the modulus. "Modulus" may be defined as the ratio of a component of stress per unit area divided by the strain along the axis of the applied force. A material has both a tensile and a compressive modulus. A material with a relatively high modulus tends to be stiff or rigid. Conversely, a material with a relatively low modulus tends to be flexible. The modulus of a material depends on its molecular composition and structure, temperature, and the strain rate or rate of deformation. Below its $T_g$, a polymer tends to be brittle with a high modulus. As the temperature of a polymer is increased to above its $T_g$, its modulus decreases.

"Ultimate strength" or "strength" of a material refers to the maximum stress that a material will withstand prior to fracture. A material may have both a tensile and a compressive strength. Ultimate strength is calculated from the maximum load applied during a test divided by the original cross-sectional area.

"Toughness" is the amount of energy absorbed prior to fracture, or equivalently, the amount of work required to fracture a material. One measure of toughness is the area under a stress-strain curve from zero strain to the strain at fracture. The units of toughness are energy per unit volume of material. See, e.g., L. H. Van Vlack, "Elements of Materials Science and Engineering," pp. 270-271, Addison-Wesley (Reading, Pa., 1989).

A brittle material is a relatively stiff or rigid material that exhibits little or no plastic deformation. As stress is applied to a brittle material, it tends to fracture at a stress approximately equal to its ultimate strength, undergoing little or no plastic deformation in the process. A polymer below its $T_g$ tends to be brittle. In contrast, a ductile material under an applied stress exhibits both elastic and plastic deformation prior to fracture. Above its $T_g$, a polymer is ductile.

A fracture may be categorized as either ductile or brittle. A relatively low amount of energy is required to fracture brittle materials. Conversely, ductile materials can absorb a relatively high amount of energy prior to fracture. Therefore, ductile materials tend to exhibit a higher toughness than brittle materials. Toughness is a desirable characteristic in implantable medical devices.

Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants, artificial bone; prostheses, vascular grafts, self-expandable stents, balloon-expandable stents, stent-grafts, grafts, artificial heart valves, and cerebrospinal fluid shunts.

"Use" of a stent includes manufacturing, assembling (e.g., crimping a stent on balloon), delivery of a stent through a bodily lumen to a treatment site, deployment of a stent at a treatment site, and treatment of a deployed stent. Both a scaffolding or substrate and a coating on a scaffolding experience stress. For example, during deployment, the scaffolding and/or coating of a stent can be exposed to stress caused by the radial expansion of the stent body. In addition, the scaffolding and/or coating may be exposed to stress when it is mounted on a catheter from crimping or compression of the stent. These stresses can cause the scaffolding and/or coating to fracture and the coating to tear and/or detach from the scaffolding. Failure of the mechanical integrity of the stent while the stent is in a patient can lead to serious consequences. For example, there is a risk of embolization caused by pieces of the polymeric scaffolding and/or coating breaking off from the stent.

FIG. 1A depicts a stent 100 comprising struts 105. Stent 100 has interconnected cylindrical rings 120 connected by linking struts 130. The embodiments disclosed herein are not limited to stents or to the stent pattern depicted in FIG. 1A. In many treatment applications, implantable medical devices, such as a stent, are preferably relatively tough and flexible since devices have varied mechanical requirements during use, both before and during treatment.

An implantable medical device may be configured to degrade after implantation by fabricating the device either partially or completely from biodegradable polymers. Polymers for use in the invention can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and may be gradually absorbed and eliminated by the body.

A biodegradable device may remain in the body until its intended function of, for example, maintaining vascular patency and/or drug delivery is accomplished. For biodegradable polymers used in coating applications, after the process of degradation, erosion, absorption has been completed, no polymer will remain on the stent. In some embodiments, very negligible traces or residue may be left behind. The duration is typically in the range of six to eighteen months, although other durations are possible.

Erosion rate of the polymer depends on a number of factors including, but not limited to, chemical composition, thickness, porosity, molecular weight, and degree of crystallinity. Several characteristics of the degradation process may be used in the invention to design the biodegradable device. These include average erosion rate, the erosion profile, the half-life of the degrading polymer, and mechanical stability of a device during the degradation process. A higher porosity increases degradation rates. Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption.

A decrease in molecular weight during biodegradation is caused by hydrolysis and/or metabolic processes. In general, hydrolysis is a chemical process in which a molecule is cleaved into two parts by the addition of a molecule of water. With respect to a bioabsorbable polymer, water takes part in the hydrolysis of ester bonds in the polymer-backbone which leads to the formation of water-soluble fragments. Consequently, the rate of degradation of a biodegradable polymer is strongly dependent on the concentration of water in the polymer. A higher concentration of water in a polymer can lead to a faster rate of hydrolysis, tending to result in a shorter degradation time of a device made from the polymer.

Many biodegradable polymers suitable for use as stent scaffoldings and coatings are relatively brittle under physiological conditions. This is particularly true for biodegradable polymers with a $T_g$ above a body temperature, such as poly (L-lactide). Therefore, for polymers like poly(L-lactide) that are brittle under physiological conditions, the fracture toughness is lower than desirable in implantable medical devices. Various embodiments of the present invention relate to increasing the fracture toughness of a polymer for use in an implantable device.

Another deficiency of some biodegradable polymers, such as poly(L-lactide), is that the degradation rate is slow and results in a degradation time outside a range of some treatment applications. In one embodiment, a preferred degradation is from six to twelve months, 12 to 18 months or 18 months to 2 years. By increasing the equilibrium content of moisture in a biodegradable polymer that degrades by hydrolysis, the degradation rate of a polymer can be increase increased. Various embodiments of the present invention include increasing the equilibrium moisture content in a polymer of a device to accelerate the degradation rate.

In some embodiments, the degradation rate of a polymer can be increased by including functional groups that tend to increase the degradation rate. For example, a functional group can be included in a polymer that has a greater affinity for water (e.g., less hydrophobic or more hydrophilic and/or one that is more hydrolytically active.)

"LPLG" has a faster degradation rate and a better fracture toughness than poly(L-lactide). However, the fracture toughness of LPLG is still lower than that desired in implantable medical devices. One way to increase fracture toughness of LPLG under physiological conditions is to blend LPLG with a polymer having relatively high fracture toughness under physiological conditions that is also immiscible and forms a discrete phase from the LPLG. The discrete phase can absorb energy arising from stress imparted to a device made from the blend to increase the fracture toughness of the device. To ensure good energy transfer between interfaces of the phases, it is important that there be sufficient bonding or adhesion between the continuous phase and discrete phase (See, Y. Wang, etc. Journal of Polymer Science Part A: Polymer Chemistry, 39, 2001, 2755-2766). Insufficient adhesion can be particularly problematic when the continuous phase and the discrete phase differ substantially in microstructure. Biodegradable polymers of high fracture toughness include polycaprolactone (PCL) and poly(tetramethyl carbonate) (PTMC). PCL and PTMC are immiscible in many polymers such as LPLG. A mixture of LPLG and either PCL or PTMC tends to separate into a LPLG continuous phase and PCL or PTMC discrete phase. Poor interfacial adhesion between the discrete and continuous phase works against the increase of fracture toughness in a polymer blend.

Furthermore, the polymer of the discrete phase can also include functional groups that tend to increase the degradation rate of the polymer blend. Such functional groups can have a high affinity for water and/or be more hydrolytically active than a majority of the functional groups that made up the continuous phase. For example, the discrete phase polymer can include glycolide monomers.

The polymer blends according to the invention have good adhesion between the discrete phase and the continuous phase, enabling various polymers to be mixed together for their respective beneficial properties. High interfacial energy transfer between the continuous phase and the discrete phase enhances the increase in the toughness of the blend. High interfacial energy transfer between phases tends to be achieved because the discrete phase is well blended or dispersed into the continuous phase, and there is good adhesion between discrete and continuous phase. Thus, the polymer blends according to the invention tends to absorb energy of a crack, thus, inhibiting crack propagation, and increasing fracture toughness of the blends.

Certain polymer blends of the invention have been found to have an increase in fracture toughness together with an increase in degradation rate. In some embodiments, the blend may include a first polymer that does not have an ideal fracture toughness and degradation rate. The first polymer may be blended with a second polymer having discrete phase segments and anchor segments that have substantially the same or the same chemical make up as the first polymer. The first polymer may form a continuous phase and the second polymer may form a discrete phase within the continuous phase. The discrete phase may be composed substantially of the second polymer's discrete phase segments. At least some of the second polymer's anchor segments may partially or completely phase-separate out from the discrete phase into the continuous phase. The second polymer's anchor segments may tend to facilitate energy transfer between continuous phase and discrete phase, thereby improving fracture toughness under physiological conditions. Furthermore, discrete phase segments of the second polymer can also accelerate the degradation rate of the first polymer.

FIG. 1B depicts a close-up view of a sidewall of a segment 110 of strut 105 depicted in FIG. 1A. FIG. 2A depicts a microscopic view of a portion 140 of segment 110 of the strut as depicted in FIG. 1B.

As depicted in FIG. 2A, portion 140 includes a continuous phase 210 and a discrete phase 220. According to the invention, there is sufficient interfacial adhesion to provide good energy transfer between continuous phase 210 and discrete phase 220 to increase fracture toughness in a device under physiological conditions.

As depicted, continuous phase 210 includes a first polymer 230. Dispersed throughout continuous phase 210 is discrete phase 220. Discrete phase 220 includes discrete phase segments 260 of second polymer 250. Discrete phase segments 260 may make up all or a substantial portion of discrete phase 220. It should also be understood by those skilled in the art that some discrete phase segments 260 may not lie entirely in the discrete phase 220, although a substantial portion of discrete phase segments 260 lie within discrete phase 220.

As described above, first polymer may not have ideal fracture toughness at physiological conditions and/or a degradation rate. For example, first polymer 230 may be brittle at physiological conditions with a $T_g$ above body temperature. PLGA can be formed to have an adequate degradation rate by adjusting the weight percent of the glycolide monomers. First polymer 230 of continuous phase 210 may be a lactide-containing polymer such as LPLG. Under physiological conditions, LPLG tends to have an acceptable degradation rate for devices, but its fracture toughness is lower than that desired in device. "Lactide-containing polymer" refers to a polymer that contains lactide moieties.

Second polymer 250 further includes one or more anchor segments 240 that are of the same or substantially the same chemical make up as first polymer 230 of continuous phase 210. FIG. 2B depicts a close-up view of a second polymer 250 having anchor segments 240 as depicted in FIG. 2A. Because anchor segments 240 are designed to have the same or substantially the same chemical make up as first polymer 230 of continuous phase 210, anchor segments 240 may be miscible with continuous phase 210. Thus, anchor segments 240 tend to phase separate out from discrete phase 220 into continuous phase 210, which enhances adhesion between discrete phase 220 and continuous phase 210. Therefore, anchor segments 240 tie or anchor discrete phase 220 to continuous phase 210.

In one embodiment, continuous phase 210 is made up of 10% glycolide and 90% L-lactide, and anchor segments 240 of second polymer 250 are also made up of 10% glycolide and 90% L-lactide. Other weight percent ratios of the glycolide and L-lactide are also possible. By selecting anchor segments 240 to have the same or substantially the same chemical make up as continuous phase 210, the interfacial adhesion between discrete phase and continuous phase is enhanced since anchor segments 240 are miscible with continuous phase 210 and phase separate into continuous phase 210. Discrete phase 220 is thereby anchored to continuous phase 210 by anchor segments 240, increasing adhesion between phases and fracture toughness in the device.

In one embodiment, discrete phase segments 260 of second polymer 250 can be selected to provide faster degradation, higher fracture toughness, and/or more flexibility (e.g., rubbery or elostomeric) under physiological conditions. Discrete phase segments 260 of second polymer 250 may also be selected so that the polymer in the discrete phase has a $T_g$ less than a body temperature. Tying or anchoring of discrete phase 220 to continuous phase 210 with anchor segments 240 results in a substantial increase in interfacial adhesion and energy transfer between continuous phase 210 and discrete phase 220. A substantial increase in interfacial adhesion and energy transfer between phases results in higher fracture toughness in structural element 110 of stent 100 compared to a stent made from first polymer 230 of continuous phase 210.

In some embodiments, discrete phase segments 260 of second polymer 250 can increase the degradation rate of the blend. In one embodiment, discrete phase segments 260 have acidic degradation by products that facilitate degradation of discrete phase 220, which also facilitates degradation of continuous phase 210. Additionally, discrete phase segments 260 have hydrophilic degradation products that increase the equilibrium level of moisture in discrete phase 220, which facilitates the degradation of discrete phase 220, which may also work to facilitate degradation of continuous phase 210.

In addition, the first polymer 230 of continuous phase 210 has acidic degradation products that enhance degradation of the blend as a whole, facilitating degradation of the discrete phase and the continuous LPLG phase.

In one embodiment, both the second polymer 250 and first polymer 230 includes glycolide, which degrades to form hydrophilic degradation products, increasing the equilibrium level of moisture in the first and second polymer. Both the acidic and hydrophilic properties of the degradation products of glycolide increase the degradation rate of an implantable medical device fabricated from the polymer blend. In addition, as the discrete phase segments and the continuous LPLG phase erode, a porous structure is created, allowing more moisture into the polymer which further increases the degradation rate of the discrete phase, also facilitating degradation of the continuous phase.

In one embodiment, the second polymer is P(GA-co-CL)-b-LPLG. In another embodiment, the second polymer is LPLG-b-P(GA-co-CL). In these embodiments, the first polymer or continuous phase is primarily or completely LPLG. The glycolide in the first polymer as well as the glycolide in the second polymer increase the degradation rate of the blend.

The caprolactone of the second polymer imparts a higher fracture toughness in the discrete phase and in the blend as a whole. (For purposes of convenience, discrete phase segments are referred to herein as P(GA-co-CL) copolymer segments of the second polymer). P(GA-co-CL) discrete phase segments can have alternating or random GA and CL monomers.

The $T_g$ of the P(GA-co-CL) segments can be tuned to a desired value by adjusting the ratio of glycolide and caprolactone monomers. For example, $T_g$ of the discrete phase may be engineered to be less than a body temperature to provide a more flexible discrete phase under physiological conditions. In addition, the LPLG of the second polymer or first polymer can be alternating or random lactide and glycolide monomers.

As mentioned above, the second polymer may have anchor segments made up of LPLG. The LPLG segments are miscible with the LPLG continuous phase. The miscibility of LPLG anchor segments of the second polymer with LPLG continuous phase enhances the interfacial energy between the discrete phase and the continuous phase. LPLG anchor segments bind P(GA-co-CL)-b-LPLG copolymer or LPLG-b-P (GA-co-CL) copolymer to the continuous phase. The anchor segments facilitate energy transfer between the continuous phase and the discrete phase when a device fabricated from the blend is placed under stress. It is believed that when a device is placed under stress, the discrete phase will absorb energy when a fracture starts to propagate through a structural element. As a result, fracture toughness of the blend, and thus the device is increased. Crack propagation through the continuous phase may then be reduced or inhibited.

In some embodiments, a blend for fabricating an implantable medical device can be a binary blend of a first polymer and a second polymer. In one embodiment, a binary blend for use in fabricating the implantable medical device may include from about 60 to 99 wt %, more narrowly 80 to 95 wt % of the first polymer having the chemical structure:

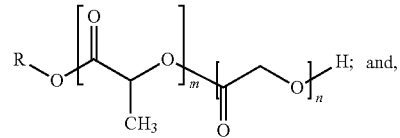

from about 1 to 40 wt %, or more narrowly 5 to 20 wt % of second polymer having the chemical structure:

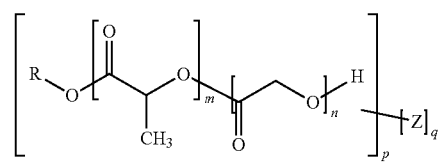

FIG. 3 conceptually illustrates the formation of the binary blend of P(GA-co-CL)-b-LPLG copolymer or "P(GA-co-CL)-b-LPLG" with LPLG copolymer or "LPLG." The P(GA-co-CL)-b-LPLG copolymer is made up of two segments: the P(GA-co-CL) copolymer segments 310 and the LPLG segments 320. The LPLG segment 320 is miscible with the LPLG continuous phase 330 as conceptually illustrated in FIG. 3. It should be understood by those skilled in the art that the illustration does not limit the copolymers to the illustrated structures.

The first polymer may be blended with the second polymer by solution blending or melt blending. In the case of solution blending, LPLG and the second polymer are dissolved in a co-solvent and then precipitated out by a non-solvent of both polymers. As for melt blending, the second polymer material is first broken up into small pieces and then blended with LPLG in an extruder, such as a single or twin screw extruder. A polymer construct such as tubing can then be formed from the blend. $T_g$ of Z may be made to be below body temperature. The first polymer forms a continuous phase while discrete phase segments Z of second polymer forms discrete phase within the continuous phase. The "p" segment of the second polymer phase-separates out from discrete phase into the continuous phase.

Z can make up discrete phase segments of the second polymer. In some embodiments, Z is a substantially or completely amorphous polymer. In some embodiments, Z is made of a rubbery material. In one embodiment, Z has a Young's Modulus between 6-8 KSi. In one embodiment, Z has two glass transition temperatures at about −20° C. and about 30° C. Upon hydrolysis, Z can form hydrophilic fragments. In one embodiment, Z is P(GA-co-CL), which degrades to form acidic and hydrophilic fragments that increase the degradation rate of second polymer having the above chemical structure.

In one embodiment, the second polymer has the chemical structure:

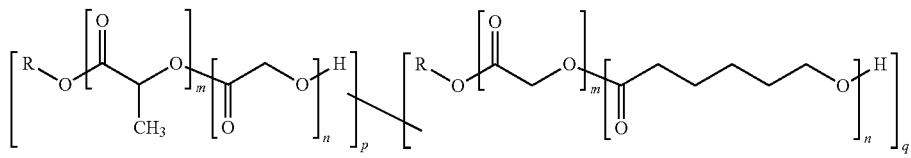

In one embodiment, the continuous phase is semi-crystalline or substantially crystalline. In this embodiment, "p" segments phase separate out of the discrete phase into the continuous phase.

In some embodiments, a polymer blend for fabricating an implantable medical device may include a rapidly eroding polymer having discrete phase segments without anchor segments. In one embodiment, the discrete phase segments are P(GA-co-CL) segments. In this embodiment, the second polymer with anchor segments is used as a compatibilizer. The discrete phase may include at least two components: (1) the rapidly eroding polymer including discrete phase segments without anchor segments and (2) a polymer with discrete phase segments and anchor segments. In one embodiment, (1) may be a substantial portion of the discrete phase and (2) may be included to facilitate the adhesion of discrete phase with continuous phase.

In one embodiment, P(GA-co-CL)-b-LPLG copolymer can be added to a mixture of LPLG and P(GA-co-CL) copolymer to form a ternary blend. In another embodiment, the LPLG-b-(GA-co-CL) copolymer can be added to a mixture of LPLG and P(GA-co-CL) copolymer to form a ternary blend. In such embodiments, the discrete phase may include P(GA-co-CL) copolymer and P(GA-co-CL) segments of the added P(GA-co-CL)-b-LPLG or LPLG-b-(GA-co-CL) while the continuous phase may include LPLG. Such ternary blends according to the invention further improve degradation and toughness of a construct. In one embodiment, both P(GA-co-CL)-b-LPLG copolymer and LPLG-b-(GA-co-CL) are added to a binary or ternary blend.

Figure 4:
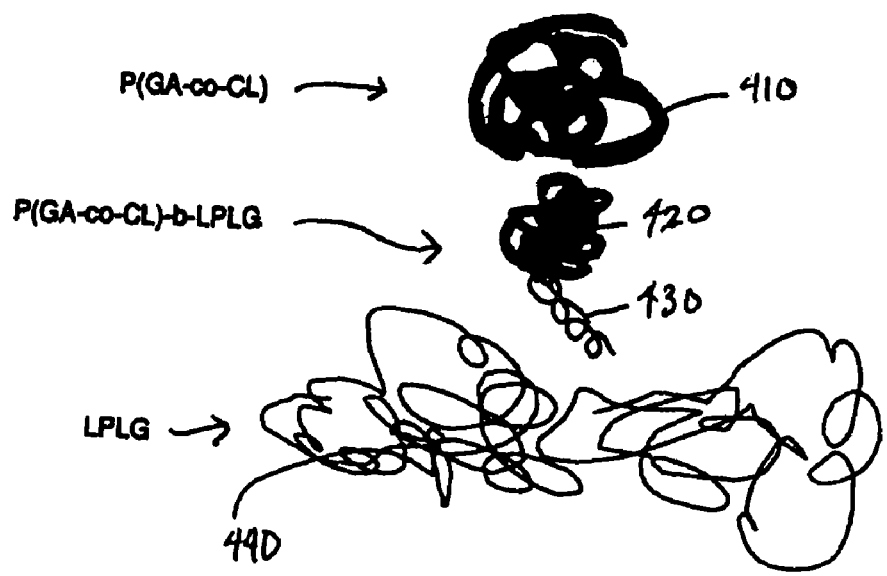
FIG. 4 conceptually illustrates a ternary blend of poly (glycolide-co-caprolactone) copolymer ("P(GA-co-CL)") with P(GA-co-CL)-b-LPLG and LPLG.

FIG. 4 conceptually illustrates the formation of the ternary blend of P(GA-co-CL) copolymer 410 with P(GA-co-CL)-b-LPLG copolymer having a P(GA-co-CL) segment 420 and a LPLG segment 430. Also, included in the ternary blend is LPLG 440. As illustrated, the P(GA-co-CL) segment 420 of P(GA-co-CL)-b-LPLG copolymer is miscible with P(GA-co-CL) copolymer 410. Also, as illustrated, the LPLG segment 430 of P(GA-co-CL)-b-LPLG copolymer is miscible with LPLG copolymer 440.

In one embodiment, a blend includes about 5-30 weight %, or more narrowly 5-20 wt % of P(GA-co-CL) copolymer and about 1 to 10 wt %, or more narrowly 2-5 wt % of P(GA-co-CL)-b-LPLG and/or LPLG-b-(GA-co-CL) copolymer in a matrix of about 60-99 wt % LPLG. In this embodiment, P(GA-co-CL)-b-LPLG and/or LPLG-b-(GA-co-CL) copolymer acts as a compatibilizer or dispersant for blending LPLG of the continuous phase with P(GA-co-CL) copolymer of the discrete phase, thereby increasing the interfacial adhesion between the discrete and continuous phases. In addition, fracture toughness of LPLG is improved. The ternary polymer blend can be prepared by solution blending or melt blending.

The P(GA-co-CL)-b-LPLG copolymer and LPLG-b-P(GA-co-CL) copolymer can be formed by solution-based polymerization. In solution based polymerization, all the reactive components involved in the polymerization reaction are dissolved in solvent. Other methods used to form P(GA-co-CL)-b-LPLG copolymer or LPLG-b-P(GA-co-CL) copolymer are also possible, such as, without limitation, melt phase polymerization.

In one embodiment, the invention provides a method of forming P(GA-co-CL)-b-LPLG copolymer. To prepare P(GA-co-CL)-b-LPLG copolymer, P(GA-co-CL) may be first prepared by solution polymerization and then employed as a macro-initiator to initiate the polymerization of the LPLG segment, as illustrated in FIG. 5. Specifically, P(GA-co-CL) segments are formed first by mixing glycolide monomers, caprolactone monomers, and a solvent to form a solution. In the solution, the glycolide and caprolactone monomers may react to form P(GA-co-CL). The method also includes adding L-lactide monomers and glycolide monomers to allow monomers to react with P(GA-co-CL) to form P(GA-co-CL)-b-LPLG.

In one embodiment, the L-lactide and glycolide monomers react in the same solution as the solution used to form P(GA-co-CL). Alternatively, the L-lactide and glycolide monomers react in a solution having a different solvent(s) as the solution to form P(GA-co-CL).

The P(GA-co-CL)-b-LPLG copolymer or LPLG-b-P(GA-co-CL) copolymer can be formed by providing a solvent system to keep the P(GA-co-CL) copolymer in solution so that the copolymer can further copolymerize with L-lactide monomers and glycolide monomers.

A large percentage of GA in P(GA-co-CL) of the second polymer is necessary to obtain a fast eroding second copolymer because the GA component in the P(GA-co-CL) segment of the second polymer has much faster degradation rate than that of CL. However, due to the low solubility of the GA monomer in most solvents, the formed P(GA-co-CL) segment which is desired to be of a high percentage in the P(GA-co-CL) copolymer may have poor solubility in most polymerization solvents. Consequently, P(GA-co-CL) copolymer as a macro-initiator can have a dramatic decrease in initiation efficiency as a macro-initiator to form the P(GA-co-CL)-b-LPLG.

In one embodiment, a macro-initiator which of a lower weight percentage of GA is used to increase solubility, thereby facilitating copolymerization. In this embodiment, LPLG segment can be formed first and then be used to macro-initiate the polymerization of GA and CL to form the P(GA-co-CL) segment of LPLA-b-P(GA-co-CL) copolymer. The synthetic route of LPLA-b-P(GA-co-CL) copolymer is illustrated in FIG. 6. In one embodiment, the first-formed LPLG segment is made to contain only 15% GA, exhibiting better solubility in many polymerization solvents. Other percentages of GA in the LPLG copolymer are also contemplated, such as 25 wt %, 20 wt %, 10 wt % and 5 wt %.

In this embodiment, LPLG-b-P(GA-co-CL) copolymer is formed by mixing the L-lactide and glycolide monomers with a solvent and catalyst to form a polymerization solution. Once LPLG is formed in the solution, glycolide monomers and caprolactone monomers are added into the solution containing the formed LPLG copolymer to form LPLG-b-P(GA-co-CL) copolymer. In one embodiment, the glycolide monomers and caprolactone monomers are added to the same solution of LPLG-formed copolymer to allow glycolide and caprolactone monomers to react with LPLG in the solution to form LPLG-b-P(GA-co-CL) copolymer. Alternatively, the glycolide monomers and caprolactone monomers are added in a solution of LPLG which includes different solvent(s).

In one embodiment, the solvent for use in synthesizing the copolymer is devoid of alcohol functional groups. Such alcoholic groups may act as initiators for chain growth in the polymer. Solvents used to synthesize the copolymer include, but are not limited to, chloroform, toluene, xylene, and cyclohexane. Initiators to facilitate the synthesis of the copolymer include, but are not limited to, dodecanol, ethanol, ethylene glycol, and polyethylene glycol. Catalysts used to facilitate the synthesis of the copolymer include, but are not limited to, stannous octoate and stannous trifluoromethane sulfonate.

It should be understood by those skilled in the art that continuous phase and discrete phase polymers other than those disclosed above and exemplified below may be used to create polymer blends of this invention for use in fabricating an implantable medical device. For example, discrete phase segments of the second polymer can be formed by polymerizing other types of monomers that provide the polymer with an increase in degradation rate and an increase in fracture toughness. For example, trimethylene carbonate monomers can be polymerized with glycolide to form discrete phase segments. Further, anchor segments and the first polymer of the continuous phase can be formed of polymers other than L-lactide, such as, for example, DL-lactide.

A stent fabricated using a polymer blend of this invention can be medicated with an active agent. A medicated stent may be fabricated by coating the surface of the polymeric scaffolding made from the blend with a polymeric carrier that includes a bioactive agent. A bioactive agent can also be incorporated into a polymeric scaffolding made from the blend.

Polymers that may be used to fabricate, coat, or modify an implantable medical device include, but are not limited to, poly(N-acetylglucosamine) (Chitin), Chitosan, poly(hydroxyvalerate), LPLG, poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(L-lactide-co-E-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

EXAMPLES

The Examples below are provided by way of illustration only and not by way of limitation. The prophetic Examples illustrate formation of LPLG-P(GA-co-CL) and P(GL-co-CL)-b-LPLG copolymer for use in fabricating an implantable medical device. This copolymer consists of two segments: the P(GA-co-CL) discrete phase segments, and the LPLG anchor segments. The parameters and data are not to be construed to limit the scope of the embodiments of the invention.

Example 1

Poly(GA-co-CL)-b-LPLG copolymer can be synthesized by forming the P(GA-co-CL) segments first. Then, P(GA-co-CL) can be used to initiate polymerization of L-lactide monomers and glycolide monomers. FIG. 5 illustrates the synthesis of P(GA-co-CL)-b-LPLG copolymer according to this embodiment. FIG. 5 shows that glycolide and caprolactone monomers can be combined in the presence of an alcohol initiator, a catalyst, and solvent to form P(GA-co-CL). L-lactide monomers and glycolide monomers was then added to the mixture to form the P(GA-co-CL)-b-LPLG copolymer.

Chloroform, toluene, xylene, or cyclohexane can be used as the solvent. Initiators can include dodecanol and ethanol. Catalysts can include stannous octoate and/or stannous trifluoromethane sulfonate.

The following two examples describe the synthesis of P(GA-co-CL)-b-LPLG copolymer for two target molecular weights. In each procedure, glycolide ("GA"), caprolactone ("CL"), and L-lactide ("LLA") are used as monomers, stannous octoate is the catalyst, dodecanol is the initiator and xylene is the solvent.

Example 1a

The following steps describe a polymerization procedure that was used to form P(GA-co-CL)-b-LPLG with a target molecular weight of 600 g/mole:

Step 1: A 2-L reaction kettle equipped with mechanical stirring was placed in a glove box which was filled with high purity nitrogen. The reaction kettle was preheated to 120° C. for 1 hour to remove moisture.

Step 2: 200 g GA, 200 g CL, 0.27 mL dodecanol, 700 ml xylene and 1.12 mL stannous octoate were added to the reaction kettle, the GA being added in 4 portions in two-hour intervals. The mixture was stirred at 120° C. for about 90 hours.

Step 3: A mixture of 170 grams LLA and 30 grams GA were then added into the reaction kettle, where 0.48 mL stannous octoate was added into the reactor and the polymerization solution was stirred at 120° C. for 70 hours.

Step 4: Once polymerization was finished, 3 L CHCl$_3$ was then added to reaction kettle to dilute the final product. The final polymerization solution was precipitated into the 8-L methanol. Then, the product was dried in vacuum at 80° C. until constant eight was achieved.

Example 1b

At the end of Step 2 in Example 1a, a small amount sample was taken out of the reaction kettle and was analyzed by Nuclear Magnetic Resonance ("NMR"). Neither GA nor CL monomer peaks were found in the $^1$H-NMR, which proved that both GA and CL monomers had been consumed to form PGA-co-PCL discrete phase copolymer. The formed P(GA-co-CL) discrete phase copolymer was a rubbery material. $^1$H-NMR of the end product of Step 3 in Example 1a showed that more than 95% LLA/GA mixture had been consumed to form the LPLG segment of P(GA-co-CL)-b-LPLG copolymer.

Example 1c

P(GA-co-CL) copolymer was also synthesized by first placing GA and CL monomers, initiator (dodecanol), catalyst (Sn(Oct)$_2$ or stannous trifluoromethane sulfonate ("Sn (OTf)$_2$,") and xylene in a reactor, as in Example 1a. The P(GA-co-CL) discrete phase copolymer was then precipitated in methanol, and dried in a vacuum oven. The P(GA-co-CL) precipitate formed can be used in a ternary blend, as described above, or used to form P(GA-co-CL)-b-LPLG.

The molecular weight of the P(GA-co-CL) discrete phase copolymer was controlled by the molar ratio of monomers to initiator. The degradation rate and toughness can be controlled by the molar ratio of GA to CL.

Example 2

The following example describes the synthesis of LPLG-co-(GA-co-CL) copolymer. In this experiment, GA, CL, and LLA were used as monomers. Stannous octoate was used as a catalyst. Dodecanol was used as an initiator. Xylene was used as a solvent.

Step 1: One 2-L reactor with a mechanical stirring rod was placed in a sealed glove box filled with high purity nitrogen. The reactor was preheated to 120° C. for 1 h and purged with high purity nitrogen to remove moisture and oxygen.

Step 2: A mixture of 170 g LLA and 30 g GA, 0.27 mL dodecanol, 700 mL xylene and 0.48 mL stannous octoate were added into reactor. The polymerization solution was then stirred at 120° C. for about 24 h.

Step 3: 260 g GA, 140 g CL, and 1.12 mL stannous octoate were then added into the reactor. The mixture was stirred at 120° C. for up to 70 h.

Step 4: Once the polymerization is finished, 3 L CHCl$_3$ is added into reactor to dilute the final product. Then the final product is precipitated into 8-L methanol and dried in vacuum at 80° C. until constant weight was achieved.

While particular embodiments of the present invention have been shown and described, it will be obvious to those skilled in the art that changes and modifications can be made without departing from this invention in its broader aspects.

The invention claimed is:

1. An implantable medical device comprising:
a structural element, wherein the structural element includes:
a continuous phase comprising a first polymer of LPLG;
a discrete phase within the continuous phase, wherein the discrete phase comprises a second polymer including discrete phase segments;
the second polymer further includes anchor segments that have the same or substantially the same chemical make up as the first polymer of the continuous phase, and at least some of the anchor segments have partially or completely phase-separated from the discrete phase into the continuous phase.

2. The device according to claim 1, wherein the implantable medical device is a stent.

3. The device according to claim 1, wherein the discrete phase segments have a T$_g$ below body temperature.

4. The device according to claim 1, wherein the discrete phase is more flexible than the continuous phase at body temperature.

5. The device according to claim 1, wherein the anchor segments are miscible with the first polymer.

6. The device according to claim 1, wherein the second polymer comprises P(GA-co-CL)-b-LPLG.

7. The device according to claim 1, wherein 5-20 wt % of the structural element comprises the second polymer.

8. The device according to claim 1, wherein the discrete phase segments degrade to acidic fragments.

9. The device according to claim 1, wherein the discrete phase segments degrade to hydrophilic fragments.

10. An implantable medical device, comprising:
a structural element fabricated of a blend that includes about 60 to about 99 wt % of a first polymer of LPLG, wherein the first polymer forms a continuous phase; and
about 1 to about 40 wt % of a second polymer, the second polymer forming a discrete phase within the continuous phase, wherein the second polymer having a T$_g$ below body temperature comprises discrete phase segments that degrade to acidic fragments,
the second polymer further comprises anchor segments having the same or substantially the same chemical make up as the continuous phase, wherein the anchor segment has phase-separated out from the discrete phase into the continuous phase.

11. The device according to claim 10, wherein the second polymer is P(GA-co-CL)-b-LPLG.

12. The device according to claim 10, wherein the anchor segment is selected from the group consisting of LPLG and materials that are miscible in LPLG.

13. An implantable medical device, comprising:
a structural element fabricated of a blend that includes:
about 60 to about 99 wt % of a first polymer of LPLG, wherein the first polymer forms a continuous phase;
about 1 to about 10 wt % of a second polymer, the second polymer forming a discrete phase within the continuous phase, the second polymer comprising discrete phase segments and anchor segments, wherein anchor segments have the same or substantially the same chemical make up as the first polymer of the continuous phase and have phase-separated out from the discrete phase into the continuous phase; and
about 5 to about 30 wt % of a third polymer having a $T_g$ below body temperature consisting essentially of discrete phase segments, wherein the third polymer degrades into fragments at least some of which are acidic.

14. The device according to claim 13, wherein the second polymer is P(GA-co-CL)-b-LPLG copolymer.

15. The device according to claim 13, wherein the anchor segments are LPLG.

16. The device according to claim 13, wherein the third polymer is P(GA-co-CL) copolymer.

17. A composition comprising:
a continuous phase comprising a first polymer of LPLG;
a discrete phase within the continuous phase, wherein the discrete phase comprises a second polymer including discrete phase segments;
the second polymer further includes anchor segments that have the same or substantially the same chemical make up as the first polymer of the continuous phase, and at least some of the anchor segments have partially or completely phase-separated from the discrete phase into the continuous phase.

18. The composition to claim 17, wherein the anchor segments are miscible with the first polymer.

19. The composition to claim 17, wherein the discrete phase comprise P(GA-co-CL) copolymer.

20. The composition to claim 17, wherein the second polymer comprises P(GA-co-CL)-b-LPLG.

21. The composition to claim 17, wherein the discrete phase segments comprise two or more of the following monomers in any proportion: glycolide, caprolactone, and trimethylene carbonate.

22. A method of forming a copolymer comprising:
mixing glycolide monomers, caprolactone monomers, a catalyst, and a solvent to form a solution, wherein the glycolide and caprolactone monomers react in the solution to form P(GA-co-CL); and adding L-lactide monomers and glycolide monomers and allowing the added monomers to react with P(GA-co-CL) to form P(GA-co-CL)-b-LPLG.

23. The method according to claim 22, wherein the L-lactide monomers and glycolide monomers are allowed to react with the P(GA-co-CL) in the presence of a solvent, wherein the solvent is the same or different solvent used to form the P(GA-co-CL).

24. The method according to claim 22, wherein the solvent is devoid of alcohol functional groups.

25. The method according to claim 22, wherein the solvent is selected from the group consisting of chloroform, toluene, xylene, cyclohexane, and any mixture thereof in any proportion.

26. A method of forming a copolymer comprising:
mixing glycolide monomers, L-lactide monomers, a catalyst, and a solvent to form a solution, wherein the glycolide and L-lactide monomers react in the solution to form LPLG; and
adding caprolactone monomers and glycolide monomers and allowing the added monomers to react with LPLG to form LPLG-b-P(GA-co-CL).

27. The method according to claim 26, wherein the caprolactone monomers and glycolide monomers are allowed to react with the LPLG in the presence of a solvent, wherein the solvent is the same or different solvent used to form the LPLG.

28. The method according to claim 26, wherein the solvent is devoid of alcohol functional groups.

29. The method according to claim 26, wherein the solvent is selected from the group consisting of chloroform, toluene, xylene, cyclohexane, and any mixture thereof in any proportion.

30. A copolymer comprising P(GA-co-CL)-b-LPLG.

31. A copolymer comprising LPLG-b-P(GA-co-CL).

\* \* \* \* \*